United States Patent
Evans, III et al.

(10) Patent No.: US 7,097,662 B2
(45) Date of Patent: Aug. 29, 2006

(54) IN-VIVO ORTHOPEDIC IMPLANT DIAGNOSTIC DEVICE FOR SENSING LOAD, WEAR, AND INFECTION

(75) Inventors: Boyd McCutchen Evans, III, Oak Ridge, TN (US); Thomas G. Thundat, Knoxville, TN (US); Richard D. Komistek, Knoxville, TN (US); Douglas A. Dennis, Littleton, CO (US); Mohamed Mahfouz, Knoxville, TN (US)

(73) Assignees: UT-Battelle, LLC, Oak Ridge, TN (US); University of Tennessee Research Foundation, Knoxville, TN (US)

(*) Notice: Subject to any disclaimer, the term of this patent is extended or adjusted under 35 U.S.C. 154(b) by 148 days.

(21) Appl. No.: 10/926,216

(22) Filed: Aug. 25, 2004

(65) Prior Publication Data

US 2006/0047283 A1  Mar. 2, 2006

(51) Int. Cl.
*A61F 2/30* (2006.01)
(52) U.S. Cl. .................... 623/18.11; 623/914
(58) Field of Classification Search ........... 623/18.11, 623/17.13, 912, 914, 20.21, 20.14, 20.32, 623/22.11
See application file for complete search history.

(56) References Cited

U.S. PATENT DOCUMENTS

| | | | |
|---|---|---|---|
| 3,915,015 A * | 10/1975 | Crane et al. ............... 73/865.4 |
| 4,503,705 A * | 3/1985 | Polchaninoff ............... 73/172 |
| 4,822,362 A | 4/1989 | Walker et al. |
| 5,197,488 A * | 3/1993 | Kovacevic ................. 600/595 |
| 5,326,363 A * | 7/1994 | Aikins ..................... 623/18.11 |
| 5,360,016 A * | 11/1994 | Kovacevic ................. 600/595 |
| 5,425,775 A * | 6/1995 | Kovacevic et al. ......... 128/898 |
| 5,456,724 A * | 10/1995 | Yen et al. ................ 623/23.49 |
| 5,470,354 A * | 11/1995 | Hershberger et al. ....... 128/898 |
| 5,719,324 A | 2/1998 | Thundat et al. |
| 5,733,292 A * | 3/1998 | Gustilo et al. .............. 606/88 |
| 5,777,467 A | 7/1998 | Arms et al. |
| 5,840,047 A * | 11/1998 | Stedham ................... 600/587 |
| 6,034,296 A * | 3/2000 | Elvin et al. .............. 623/16.11 |
| 6,143,035 A * | 11/2000 | McDowell ............... 623/22.11 |
| 6,245,109 B1 * | 6/2001 | Mendes et al. ........... 623/18.11 |
| 6,523,392 B1 | 2/2003 | Porter et al. |
| 6,553,681 B1 * | 4/2003 | Ekholm et al. ............... 33/551 |
| 6,567,703 B1 * | 5/2003 | Thompson et al. ............ 607/60 |
| 6,573,706 B1 | 6/2003 | Mendes et al. |
| 6,583,630 B1 | 6/2003 | Mendes et al. |
| 6,610,096 B1 * | 8/2003 | MacDonald ............. 623/18.11 |
| 6,706,005 B1 * | 3/2004 | Roy et al. ................... 600/594 |
| 2002/0102743 A1 | 8/2002 | Majumdar et al. |
| 2002/0130673 A1 * | 9/2002 | Pelrine et al. .............. 324/727 |
| 2003/0069644 A1 * | 4/2003 | Kovacevic et al. ...... 623/20.32 |
| 2004/0019384 A1 * | 1/2004 | Kirking et al. .......... 623/20.14 |

(Continued)

OTHER PUBLICATIONS

P.F. Sharkey et al., "Why are Total Knee Anthroplasties Failing Today?," Clin Orthop, 2002, pp. 7-13, vol. 404.

(Continued)

*Primary Examiner*—Alvin J. Stewart
(74) *Attorney, Agent, or Firm*—Kirk A. Wilson

(57) ABSTRACT

A device for providing in vivo diagnostics of loads, wear, and infection in orthopedic implants having at least one load sensor associated with the implant, at least one temperature sensor associated with the implant, at least one vibration sensor associated with the implant, and at least one signal processing device operatively coupled with the sensors. The signal processing device is operable to receive the output signal from the sensors and transmit a signal corresponding with the output signal.

31 Claims, 6 Drawing Sheets

U.S. PATENT DOCUMENTS

| | | | |
|---|---|---|---|
| 2004/0080319 A1 | 4/2004 | Merrill | |
| 2005/0010302 A1* | 1/2005 | Dietz et al. | 623/20.21 |
| 2005/0165317 A1* | 7/2005 | Turner et al. | 600/486 |
| 2005/0273170 A1* | 12/2005 | Navarro et al. | 623/17.13 |
| 2006/0004431 A1* | 1/2006 | Fuller et al. | 607/116 |

OTHER PUBLICATIONS

T. K. Fehring, et al., "Early Failures in Total Knee Orthoplasty," Clin Orthop, 2001, pp. 315-318, vol. 382.

J. F. Brick, et al., The Patellofemoral Component of Total Knee Arthroplasty, Clin Orthop, 1988, pp. 163-178, vol. 231.

G. Bergmann, et al., "Hip Joint Loading During Walking and Running Measured in Two Patients," J of Biomechanics, 1993, pp. 969-990, vol. 26, Issue 8.

G. Bergman, et al., "Frictional Heating of Total Hip Implants, Part I Measurements in Patients" J of Biomechanics, 2001, pp. 421-428, vol. 34.

G. M. Kotzar, et al., "Telemeterized In Vivo Hip Joint Force Data: A Report on Two Patients After Total Hip Surgery," J of Ortho Research, 1989, pp. 621-633, vol. 9, Issue 5.

D. T. Davy, et al., "Telemetric Force Measurements Across the Hip after Total Arthroplasty," J of Bone and Joint Surgery, 1988, pp. 45-50, vol. 70-A, Issue 1.

K. R. Kaufman, et al., Instrumented Implant for Measuring Tibiofemoral Forces, J of Biomechanics, 1996, pp. 667-671, vol. 29, Issue 5.

S. J. G. Taylor, et al., "Forces and Moments Telemetered from Two Distal Femoral Replacement During Various Activities," J of Biomech, 2001, pp. 839-848, vol. 34.

\* cited by examiner

IN-VIVO ORTHOPEDIC IMPLANT DIAGNOSTIC DEVICE FOR SENSING LOAD, WEAR, AND INFECTION

STATEMENT REGARDING FEDERALLY SPONSORED RESEARCH

This invention was made with Government support under Contract No. DE-AC05-00OR22725 awarded to UT-Battelle, LLC, by the U.S. Department of Energy. The Government has certain rights in this invention.

TECHNICAL FIELD

This invention relates to diagnostic medical instruments and procedures, and more particularly to implantable devices and methods for monitoring physiological parameters.

DESCRIPTION OF THE BACKGROUND ART

The procedure of replacing knee joints affected by osteoarthritis and other disease originated in the early 1960's. The success rate of this procedure improved tremendously in the following decades. However, there are an estimated 22,000 knee replacements revised yearly. Revision in other joint replacement surgery is common as well. There is still the need to improve the mechanical aspects and wear characteristics of the knee prosthesis, such that regardless of the age of the patient, any prosthesis will be expected to last a lifetime. The need also exists to improve the tools with which physicians can perform diagnostics on implanted devices in the general patient.

Much of the problem in designing prosthesis for the total knee arthroplasty (TKA) procedure lies in the fact that there is almost no in vivo data on the load conditions available. Much of the data that is available is derived from mathematical models or cadaver studies. A very limited amount of data is available using instrumented implants. There are concerns about the reliability of modeling data due to the inability to verify the modeling data with actual data and it is difficult to produce the forces and motions existing in a human using a cadaver. Most of the systems that have been used to collect data on living humans have been used on a small number of subjects and therefore the applicability of this data to a large population is questionable, and these systems have not been designed for use in a large number of devices over a long period of time, or to be manufactured on a commercial basis.

Complications resulting from patellofemoral resurfacing have been attributed as many as half of all revision total knee arthroplasties (TKA). Most complications are caused by errors in surgical technique, poor prosthetic design, or excessive patellofemoral loads of up to seven or eight times body weight during certain activities such as squatting. In many cases, however, poor knee kinematics and an inadequate understanding of the forces exerted on the prosthetic components play a key role in the wear, mal-alignment, or design flaws associated with the complications described below.

Patellofemoral complications are a prominent cause of failure in TKA. The most common TKA complication is patellofemoral subluxation (dislocation of the patella to either the medial or lateral side of the knee), which occurs in up to 29 percent of some series, resulting in patellofemoral pain and crepitus, component wear, failure, loosening and/or fracture. Other complications that lead to patellar component failure are malposition of the femoral, tibial or patellar components, poor implant design, patellar fracture, mal-alignment, inadequate patellar resection, avascular necrosis, and revision TKA.

Such complications induce many surgeons to avoid patellar resurfacing in patients with osteoarthritis and good remaining articular cartilage. However, several studies indicate increased patellofemoral problems without resurfacing, and secondary resurfacing after primary TKA with a failed nonresurfaced patella has proven inferior to resurfacing at the time of primary TKA.

In a 2002 review of all (212) revisions at one institution between 1997 and 2000, Sharkey et al. attributed early failures to infection (25.4%), loosening (16.9%), instability (21.2%), extensor mechanism deficiency (6.6%), avascular necrosis of the patella (4.2%), and isolated patella resurfacing (0.9%). The prevalent causes of overall failure were polyethylene wear (25%), aseptic loosening (24.1%), instability (21.2%), infection (17.5%), arthrofibrosis (14.6%), malalignment (11.8%), extensor mechanism deficiency (6.6%), patella necrosis (4.2%), periprosthetic fracture (2.8%), and the need to resurface the patella (0.9%). Malalignment was present in 11.8% of all implants requiring revision. Fehring, et al, in a survey of 440 patients, found similar results. These studies did not report patella-femoral complications individually, however revision of the patella-femoral component has been reported in as many as 50% of revisions.

Instrumentation of orthopedic implants has been performed by a few researchers on a small number of patients to measure the loads between the mating components. Most of this research has been performed on hip prosthesis instrumented with strain gages. G. Bergman has published research on hip loading using forces measured using strain gages. His instrumented prosthesis is powered using an inductive coil, and the measurements are sent to a personal computer using an RF telemetry system. The power for this system is generated using an inductive coil worn around the patient's leg during testing. Bergman reported loads from two patients. His data showed that joint loads range from 2.8 times body weight (BW) to 4.8 BW depending on walking speeds. These loads increased to 5.5 BW with jogging, and stumbling caused hip loads to go as high as 7.2 BW.

Similar research on hip implants has been performed by Davy and Kotzar. A similar hip prosthesis was implanted in two patients. Davy and Kotzar measured peak loads of 2.1–2.8 BW during gait and a maximum value of 5.5 BW during periods of instability during single leg stance.

K R Kaufman has reported on the design of an instrumented tibial component of TKA knee prosthesis. This device consists of a specially machined tibial tray. The tibial tray is hollowed out in Kaufman's research to form a diaphragm which is instrumented with strain gages. This device is used to determine the tibiofemoral loads. No reference as to power source or data collection method is given. We are unaware of any data collected or published using this device.

Taylor and Walker measured the forces in the distal femur in two subjects with an instrumented distal femoral replacement (DFR). The DFR was instrumented with strain gages and as in other devices inductive coupling was used to power the implant. The DFR is a large prosthesis which replaces the majority of the femur. The forces measured were as high as 3.6 BW for jogging. This device was capable of measuring the axial torque on the femur. Bending moments were greatest about the antero-posterior axis (varus-valgus) at 9.8 BW-cm.

Post-operative infection is a particularly serious threat occurring in total joint replacement and organ transplant procedures. In a survey of joint replacement surgeries performed at the Mayo Clinic in the years 1969–1996, deep wound infection (DWI) occurred in 2% of 16,035 primary total knee arthroplasty (TKA) and 1.3% of 23,519 total hip arthroplasty (THA) patients. Patients that develop DWI are at serious risk for loss of limb/organ or mortality. The estimated cost of treating post-surgical infections in orthopedic procedures alone is over $340,000,000 per year (Hansen 1999).

Recent drug-discovery research has focused on a new method of producing oligonucleotides called aptamers. These short (15–30 base) single-stranded, oligonucleotides are more stable than antibodies. Aptamers have protein recognition and binding characteristics similar to antibodies, and can be engineered to target virtually any molecule. Drug discovery researchers have examined using aptamers to aid the immune system in recognizing foreign invaders in a method similar to antibodies.

Research using instrumented implants has been fairly limited as shown in the preceding paragraphs. The research that has been done has been performed to gain an understanding of joint loading conditions has consisted of on a statistically small population. The number of patients and data gathered is given to illustrate the variation in data and statistically small population. The following paragraphs will discuss recent patents in this field.

U.S. Pat. No. 6,706,005 to Roy et al., issued on Mar. 16, 2004, teaches a device for measuring only loads incident on the device using microcantilevers. No teaching of load derivation, temperature measurement, or infection sensing is present.

U.S. Pat. No. 5,470,354 with inventors Hershberger; Troy W. (Warsaw, Ind.); Booth, Jr.; Robert E. assigned to Biomet, Inc. describes a device and a method for determining proper alignment and placement of implant components during joint reconstruction surgery. This patent is primarily aimed for use in the knee joint. Provisional components are often used in joint replacement surgery to determine the proper sizes and relationships of the final components used in joint arthroplasty. In this patent, provisional components are instrumented with force transducers. These transducers are used to determine the forces in the joint and to aid in determining the proper size component and how to balance the forces in the joint. Force transducers are connected to computers and provide readings of the location and magnitude of the forces generated in the joint when the joint is moved through its range of motion during surgery. Therefore, this system is utilized for Intraoperative assessment but is not of value in assessing in vivo, weight-bearing loads after total knee implantation.

U.S. Pat. Nos. 5,360,016 and 5,197,488 invented by Nebojsa Kovacevic is assigned to NK Biotechnical Engineering Company. This patent describes a force transducer for a joint prosthesis. The transducer in this patent is similar to the one described in the research paper published by Kaufman and Kovacevic in 1996. The transducer in this paper is a highly modified tibial tray TKA component. A series of cavities are machined on the superior side of the tibial tray such that they become flexible members. Strain gages are attached to each flexure member to provide a signal corresponding to the force applied to the flexure member. No mention is made of supply power, signal conditioning, or data collection.

U.S. Pat. No. 5,425,775 issued to Kovacevic; Nebojsa (Plymouth, Minn.) and assigned to NK Biotechnical Engineering Company Nov. 2, 1993 describes a method and apparatus for measuring the forces acting on a patella includes a patella sensor comprising a sensor, a sensor cover, and multiple strain gages. This sensor consists of a significantly modified patellar insert, similar to U.S. Pat. Nos. 5,360,016 and 5,197,488 by Kovacevic for a tibial tray force transducer. This system consists of a large metal diaphragm (sensor cover) or deformable member covering the entire diameter of the patellar implant. The sensor cover is attached to the sensor and has an outer surface that is in contact with a femoral insert. The sensor cover transmits the forces acting on its outer surface to the sensor. The sensor has a plurality of strain gages mounted thereon to measure the forces acting on the sensor cover. A requirement of this sensor is a metal-backed patellar prosthesis which has been shown in multiple studies in the orthopedic literature to have inferior long term clinical results and relatively high complication rates. It also seems a requirement that a larger amount of material be resected from the patient's patella than would be with a traditional patellar insert. No mention is made of how an entire measurement system from signal conditioning to operating power is derived for this sensor. No examples of use of this device or similar devices were found in the research literature.

U.S. Pat. No. 4,822,362 Walker; Peter S. (Weston, Mass.); Ewald; Frederick C. (Weston) A prosthesis and a surgical procedure (process) therefore are provided having a relatively thin plate fitted to a resected portion of the tibial plateau with the plate fitting uniformly around a major portion of the calcareous bone of the cortical wall. A pin on the under side of the plate aligned substantially with the axis of the intramedullary canal of the tibia fixes the plate against transverse relative motion between the plate and plateau, and blades or keels also on the under side of the plate are aligned maximum density (strength) of the cancellous bone of the plateau and fix the plate against rotation relative to the plateau. The surgical procedure of the invention employs a template to assure approximate positioning, and exact interrelationship between the plate and the fixing means.

References cited and herein incorporated by reference are:
1. Sharkey P F, Hozack W J, Rothman R H, Shastri S, Jacoby S M., "Why are total knee arthroplasties failing today?", *Clin Orthop* 404: 7–13, 2002.
2. Fehring T K, Odum S, Griffin G L, Mason J B, Nadaud M., "Early Failures in Total Knee Orthoplasty", *Clin Orthop* 382: 315–318, 2001.
3. Brick J F, Gutmann L., "The patellofemoral component of total knee arthroplasty", *Clin Orthop* 231: 163–178, 1988.
4. Bergmann G, Graichen F, Rohlmann A., "Hip Joint Loading During Walking and Running Measured in Two Patients", Journal of Biomechanics 26 (8): 969–990, 1993.
5. Bergman G, Graichen F, Rohlmann, A, Verdonschot N, van Lenthe G H. Frictional heating of total hip implants. Part 1. measurements in patients. Journal of Biomechanics 34: 421–428, 2001.
6. Kotzar G M, Davy D T, Goldberg V M, Heiple K G, Gerilla J, Heiple K G Jr, Brown R H, Burstein A H. Telemeterized In Vivo Hip Joint Force Data: A Report on Two Patients After Total Hip Surgery. Journal of Orthopaedic Research 9 (5): 621–633, 1989.
7. Davy D T, Kotzar G M, Brown R H, Heiple K G, Goldberg V M, Heiple K G Jr., Berilla J, Burstein A H. Telemetric Force Measurements Across the Hip after Total Arthroplasty. Journal of Bone and Joint Surgery 70-A (1): 45–50, 1988.

8. Kaufman K R, Kovacevic N, Irby S E, Colwell C W. Instrumented Implant for Measuring Tibiofemoral Forces. Journal of Biomechanics. 29 (5): 667–671, 1996.
9. Taylor S J G, Walker P S. Forces and Moments Telemetered from Two Distal Femoral Replacements During Various Activities. Journal of Biomechanics 34: 839–848, 2001.
10. U.S. Pat. No. 5,470,354. Force sensing apparatus and method for orthopaedic joint reconstruction. Inventors: Hershberger; Troy W. (Warsaw, Ind.); Booth, Jr.; Robert E. Assignee: Biomet, Inc.
11. U.S. Pat. No. 5,360,016 Force transducer for a joint prosthesis. Inventor: Nebojsa Kovacevic Assignee: NK Biotechnical Engineering Company. Nov. 1, 1994.
12. U.S. Pat. No. 5,197,488 Knee joint load measuring instrument and joint prosthesis Inventor: Nebojsa Kovacevic Assignee: NK Biotechnical Engineering Company. Mar. 30, 1993.
13. U.S. Pat. No. 5,425,775. Method for measuring patellofemoral forces. Inventor: Nebojsa Kovacevic Assignee: NK Biotechnical Engineering Company. Mar. 30, 1993.
14. U.S. Pat. No. 4,822,362 Process and apparatus for tibial plateau compenent Inventors: Walker; Peter S. (Weston, Mass.) and Ewald; Frederick C. (Weston, Mass.).
15. U.S. Pat. No. 6,706,005 Apparatus and method for assessing loads on adjacent bones; issued Mar. 16, 2004 to Roy et al.

SUMMARY OF THE INVENTION

This invention is a sensor system for use in orthopedic devices. The sensor suite allows the external monitoring of the forces between the orthopedic or other medical devices and the patient, the force or pressure between a joint replacement component and the underlying bone, the forces internal to the medical device, the amount of wear of the orthopedic device, the vibrational characteristics of the medical device, frictional heating, and internal infection. Examples of medical devices with which this invention can be used consist of, but are not limited to the following: the tibial, femoral, or patellar components used in total knee replacement, the femoral or acetabular components used in total hip implants, the scapular or humeral components in shoulder replacement, the tibia and talus in ankle replacement, and between the vertebral bodies in the lumbar and cervical spine disk replacements. Monitoring the forces in the joint will allow the manufacturers of implants to better understand the kinematics of the joint and develop more reliable implants. Data from in vivo sensing elements will provide accurate boundary conditions for mathematical models the affected joint. Also, this invention will allow the clinician to perform in vivo monitoring and diagnostics of orthopedic and other implants for the general patient in order to understand the effects of load magnitude, load imbalance, wear, and the presence of infection.

The invention consists of a series of a microscopic sensing element or elements fabricated using semiconductor or MEMS (microelectromechanical systems) fabrication technology. One embodiment of these sensors is an array of microcantilevers sensing elements. The sensor is self-powered using piezoelectric elements or externally powered by either electromagnetic induction, radio frequency (RF) induction or batteries. The sensor uses RF technology or other means to remotely transmit data. A passive version exists in which RFID technology is used to passively power the device and transmit the data. In the most robust embodiment of this sensor, the sensor package also incorporates a vibration sensing element, a temperature sensing element, a chemical sensing element, and an ultrasonic transmitter-receiver in the electronics package. These elements allow for the determination of the presence of infection and the determination of the thickness of the bearing surface of the implant. Other embodiments of the sensor elements are available for sensing different loads including piezoelectric sensing elements and double supported microbeam technology.

One embodiment of the device provides in vivo diagnostics of loads, wear, and infection in orthopedic implants. The device has at least one load sensor associated with the implant for generating an output signal in response to and indicative of normal and transverse loads being applied to the implant; and at least one temperature sensor associated with the implant for generating an output signal in response to and indicative of a temperature proximate said implant; and at least one vibration sensor associated with the implant for generating an output signal in response to and indicative of a vibration proximate the implant; and at least one signal processing device operatively coupled with at least one load, temperature, and vibration sensor and being operable to receive output signals from at least one load, temperature, and vibration sensor and to transmit a signal corresponding with the output signal.

DETAILED DESCRIPTION OF THE PREFERRED EMBODIMENTS

This invention measures the forces and pressures existing between the human body or limb and prosthetic implants. A further advantage is to measure the patellofemoral bearing surface forces including forces in the coronal and saggital planes of the limb. Another advantage of this invention is to measure the wear in orthopedic prosthesis. A further advantage of this invention is to measure indicators of infection in orthopedic implants. Yet another advantage of this invention is to measure the vibration characteristics of orthopedic implants. Another advantage of this invention is to measure frictional heating in orthopedic implants. The advantages of this invention are accomplished by the novel application of micromachined cantilever or "simply-supported" beams. These beams have been shown to provide response to each of the previously mentioned advantages. Microcantilever beams are uniquely applicable to these measurement scenarios due to their small size, ease of determining measured quantity, and low power consumption. The patellar resurfacing prosthesis is used to illustrate this invention, however the concepts set forth in the patellar prosthesis are easily utilized in a hip, shoulder, tibial or femoral components of the TKA prosthesis, or other orthopedic devices and prosthesis.

Figure 1:
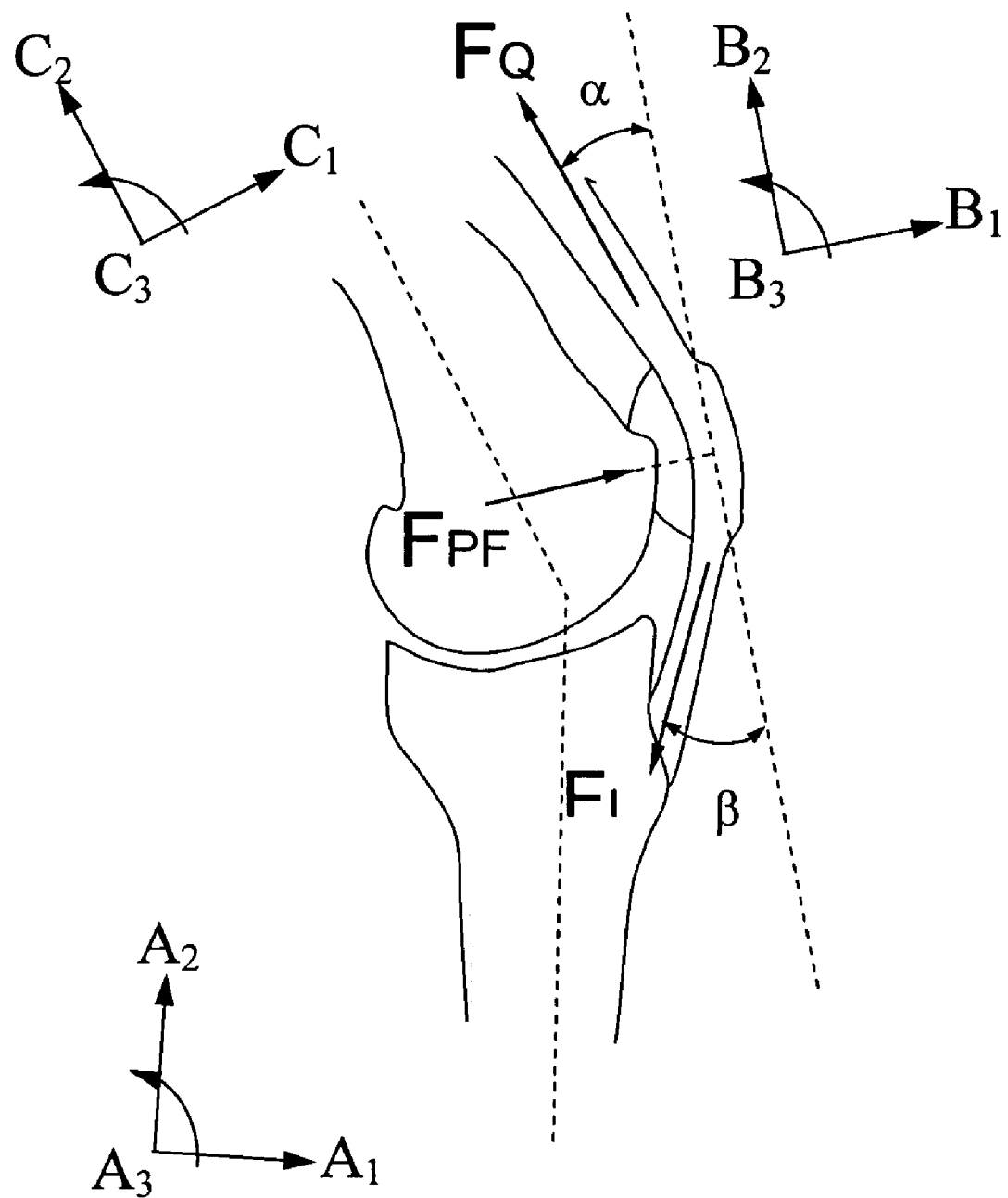
FIG. 1 is a force diagram showing the three force system acting on the patella.

In the manner in which this sensor is applied to the patellar prosthesis, not only will the forces between the prosthesis and the underlying patellar bone be measured, but tibiofemoral forces can be deduced as well as the muscle forces from the quadriceps and the force in the patellar tendon will be determined as well. This is because the patella has a system of three forces acting on it. These forces are the force supplied by the quadriceps, the reaction force supplied by the patellar tendon, and the bearing surface interaction force between the patella and the femur. Measurement of one of these forces allows solution of the other two forces. The ability to measure muscle forces in the human body has eluded the researcher for centuries. The three force system of forces in the patella and the equations for solving those forces are illustrated in FIG. 1.

The equations for solving the forces are:

$$F_{PF} = F_Q \sin(\alpha) + F_L \sin(\beta)$$

$$F_Q \cos(\alpha) = F_L \cos(\beta)$$

$$F_Q = \frac{F_{PF}}{\sin(\alpha) + \cos(\beta)\tan(\alpha)}$$

$$F_L = \frac{F_{PF}}{\sin(\beta) + \cos(\alpha)\tan(\beta)}$$

where $F_Q$ represents the quadriceps force, $F_L$ represents the patellar ligament force, and $F_{PF}$ represents the patellofemoral contact force. Frames A, B, and C are reference frames commonly used in dynamical modeling. The A frame represents the orientation of the tibia, the B frame represents the orientation of the patella, and the C frame represents the orientation of the femur. $\alpha$ represents the angle between the $B_2$ axis and the quadriceps tendon and specifies the direction of the quadriceps force. $\beta$ represents the angle between the patellar ligament and the $B_2$ axis and specifies the direction of the force between the tibia and the patella. The patellofemoral joint reaction force is assumed to be along the $B_1$ axis.

The load measuring device in this invention is configured not only to measure the normal patello-femoral bearing surface loads, i.e. the normal pressure internal to the implant, but also measures the transverse load (or pressure) which in the case of the patella is indicative of muscle imbalance, malalignment, and potential subluxation. This invention feature is distinct from prior load measuring devices that incorporate only a single sensor capable of measuring the forces in a single direction. In the case of an instrumented tibial tray, the variation of the load over the sensor is indicative of the alignment, muscle/ligament imbalance, improper mechanics, etc. Even in the spine, it is beneficial to measure the load in multiple directions or locations.

Several methods are available for detecting the motion of the microcantilever beam. Common methods of measuring this motion are based on the application of specific coatings to the surface of the cantilever beams. These can be piezoresistive coatings whose resistance changes as a function of bending or piezoelectric coatings which emit charge when the beam undergoes a dynamic load. Another common method of determining the beam bending is to use the cantilever beam itself as one of the plates in a parallel plate capacitor and correlating the change in capacitance with deflection. Other methods are available for measuring this deflection, such as optical methods, but the previously mentioned methods are the most suited to this application at this time.

Figure 2:
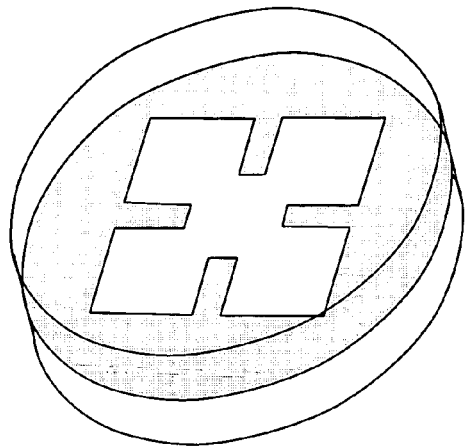
FIG. 2 is an illustration of a curved embodiment of the micro load cell using encapsulant stiffness for tuning.
Figure 2:
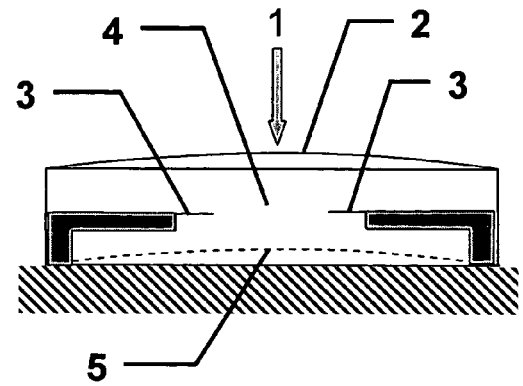

For measuring the forces in the patella, the beams may be encapsulated in an intermediate package, or otherwise attached to the surface of the prosthesis. In the preferred embodiment, the beams are encapsulated in a polymer or elastomeric material. This intermediate material can be used to "tune" the response of the device such that the optimum response range of the microcantilever device corresponds to the load range expected in the experimental conditions. The polymer material has a slight convex side and a slight concave side to improve the transmittal of forces through the package. This package is mounted between the surface of the prosthesis and the naturally occurring bone. FIG. 2 shows a diagram of this embodiment. A load 1 imposed on the concave surface 2 of a load cell is sensed by a microcantilever sensor 3 disposed in an encapsulant 4. The load cell also has a concave surface 5. The load cell uses at least one microcantilever sensor in the sensor suite. A single array or multiple arrays of sensors can also be used.

Figure 3:
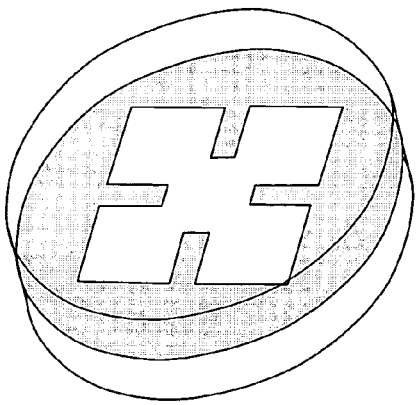
FIG. 3 is an illustration of a non-curved embodiment of the micro load cell using packaging stiffness for tuning.
Figure 3:
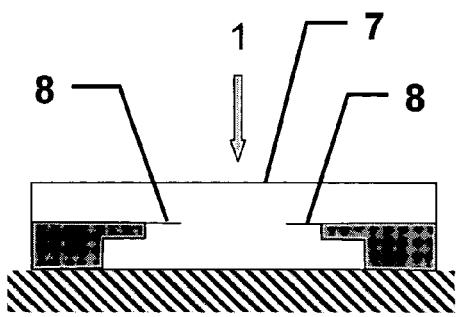

Another embodiment shown in FIG. 3 illustrates a micro load cell package using no convex or concave surfaces, but relies on the use of a stiffer packaging material 7 to support the cantilevers around the outside, such that there is a differential strain towards the center of the device. A load 1 imposed on the packaging material 7 disposed around a microcantilever sensor 8 is sensed by the load cell. The Young's modulus (stiffness) E of the packaging material 7 is used to tune the response of the micro load cell and is greater than the stiffness E of the internal components. This packaging scheme would possibly be preferred in environments where the package itself might be surrounded with cement or other adhesive in an uncontrolled manner, thereby negating the effects of the concave and convex surfaces. This package is on the order of three millimeters in diameter and a millimeter or less in height, and amounts to the equivalent of a micro load cell.

Figure 6:
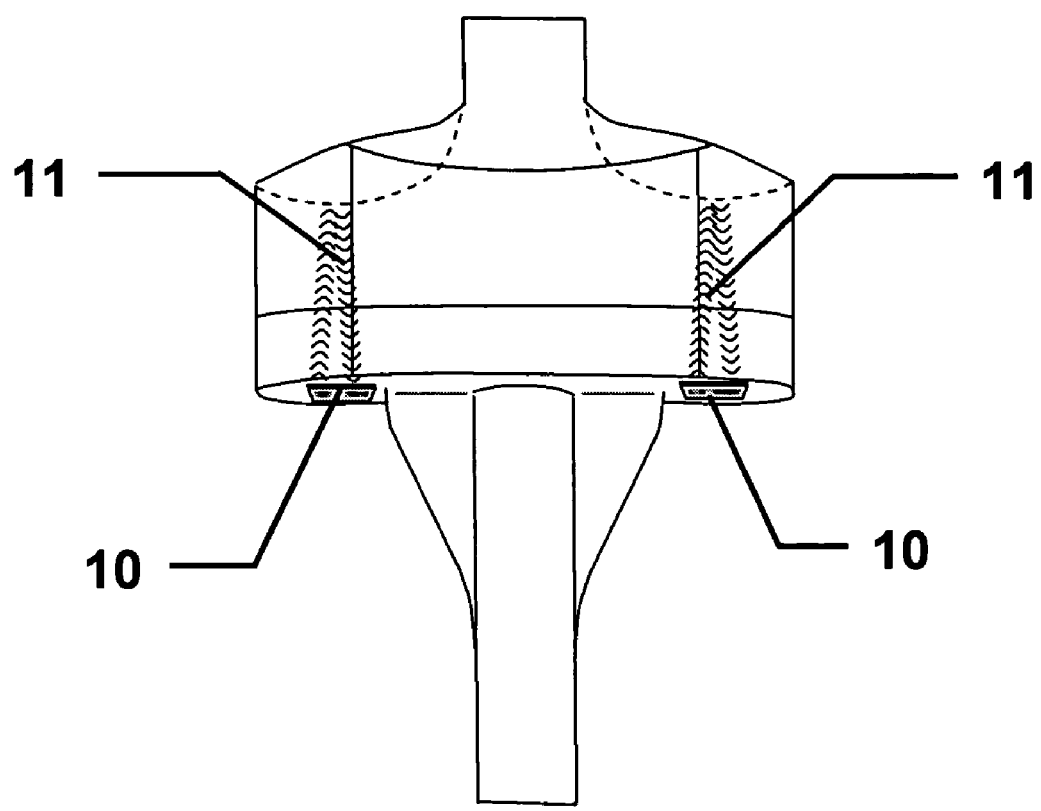
FIG. 6 is an illustration of an ultrasonic device in patellar prosthesis.
Figure 7:
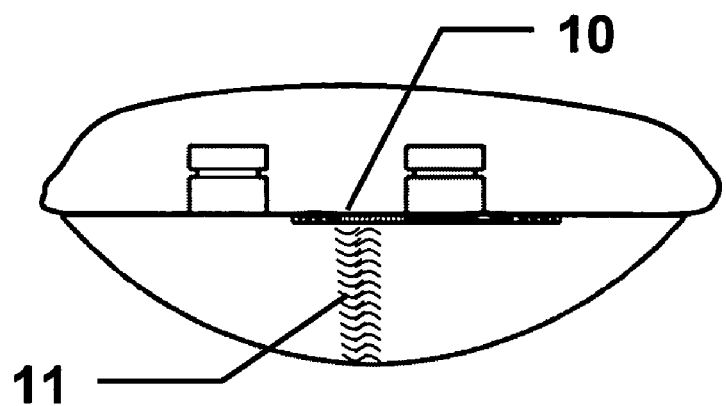
FIG. 7 is an illustration of an ultrasonic device in a tibial prosthesis.

Another advantage of this invention is to measure the wear existing in orthopedic implants. This invention performs this task by incorporating an ultrasonic transmitter and receiver in its signal processing chip as shown in FIGS. 6 and 7. The ultrasonic transmitter/receiver is in the form of a piezoelectric material incorporated in the ultrasonic transceiver element 10. A burst of ultrasonic energy 11 is emitted and received allowing the thickness of the wear surface to be measured by measuring the time for the energy to reflect off of the back surface or surfaces of the material. In the preferred embodiment a single element is utilized as the transmitter and the receiver, another embodiment is to use different elements. Also in the preferred embodiment, the transducer/receiver is fabricated from piezoelectric material using surface micromachining techniques, and an alternative embodiment is to use surface micromachined capacitive structures as resonant cavities to produce and receive the ultrasonic energy. The principles of ultrasonic thickness measurement rely on knowing the speed of sound in a material. Equation 1 shows the relationship between the thickness of the material of interest, d, the bulk modulus of the material of interest, B, the density of the material, $\rho_0$, and the time between the emission and reception of the pulse of acoustic energy.

$$d = \frac{1}{2} t \sqrt{\frac{B}{\rho_0}}$$

This aspect of the invention is illustrated in a tibial TKA component and a patellar prosthesis component as shown in FIGS. 6 and 7 respectively. In the application of the tibial tray, the preferred embodiment places the sensor package underneath the tibial tray, such that it does not interfere with the polyethylene insert of mobile bearing prosthesis. The sensor package could easily be located underneath the bearing surface in fixed bearing components, or molded into the polyethylene component as well.

Microcantilevers have been used to measure very precise changes in temperature. Often these cantilevers are coated with a material, such as gold, which causes the microcantilever to undergo bimaterial bending. A temperature sensing cantilever will be included in the prosthesis diagnostic sensor suite. Measurement of temperature of the prosthesis will give indication of the presence of conditions such as infection or noninfectious inflammatory syndromes causing joint synovitis such as rheumatoid arthritis, soft tissue impingement or friction syndromes, etc. if the patient is not currently in an active mode. The measurement of temperature can also be used to measure frictional heating of the prosthesis component. Frictional heating is another indication of wear and has been suggested as a cause in prosthesis failure.

Infection is one of the most clinically devastating complications of any major surgical procedure. Post-operative infection, clinically referred to as deep wound infection (DWI), is a particularly serious threat occurring in procedures such as total joint replacement, organ transplant, and other surgical procedures in which a foreign material is implanted into the body. The presence of the foreign material allows bacterial proliferation which is more difficult to eradicate with traditional antibiotic treatment regimens than in infections in which foreign materials are not present. Subsequently, an infected total joint replacement requires implant removal in order to eradicate the infection in a substantial percentage of cases. One of the keys of infection eradication without implant removal is early recognition of the infection. While certain bacteria grow rapidly, creating clinical signs of infection early after inoculation, others create less clinical signs making early diagnosis difficult. Any sensing device which would provide an early signal to the physician of the presence of infection would result in higher infection cure rates and less patient morbidity. Cellular signaling responses to infection are represented by changes in electrical charge caused by increases in calcium and other ions and increases in concentrations of chemical and biological attractants of macrophages, T-lymphocytes, and neutrophils. These attractants include: c-reactive proteins, activated factor XII, serotonin, and epinephrine. During the immune response to infection, macrophages produce cytokines which in turn signal the production of proteins that participate in inflammation and immune response. Four families of cytokines produced early in the immune response are tumor necrosis factor-α, interleukin-1, interleukin-6, and interferon. Other families of cytokines are also present in the immune response.

Cellular signaling is determined by incorporating microcantilevers coated with antibodies specific to biological attractant molecules and microcantilevers coated with aptameric receptors (synthetic RNA molecules or single-stranded DNA molecules) specific to cytokines (cellular signaling proteins) in tissue culture or a representative sample in which endothelial, mast, neutrofil, macrophage, and osteoblast cells are stressed by infectious agents. This invention advances the state of the art in biological sensing on several fronts through detection of multiple mechanisms of cellular signaling, increasing in the understanding of the response to infection, and the incorporation of microcantilever technology for in vivo sensing applications.

One embodiment of the invention positions the infection sensor to monitor for infection markers in the drainage tube effluent from implants and other surgical procedures. This embodiment will detect specific bacteria indicative of infection.

This invention is also beneficial in the detection of sepsis and septic shock, the leading cause of death in intensive care units. The early detection of infection and the identification of the infectious process will lead to more effective treatment of infectious processes.

Figure 8:
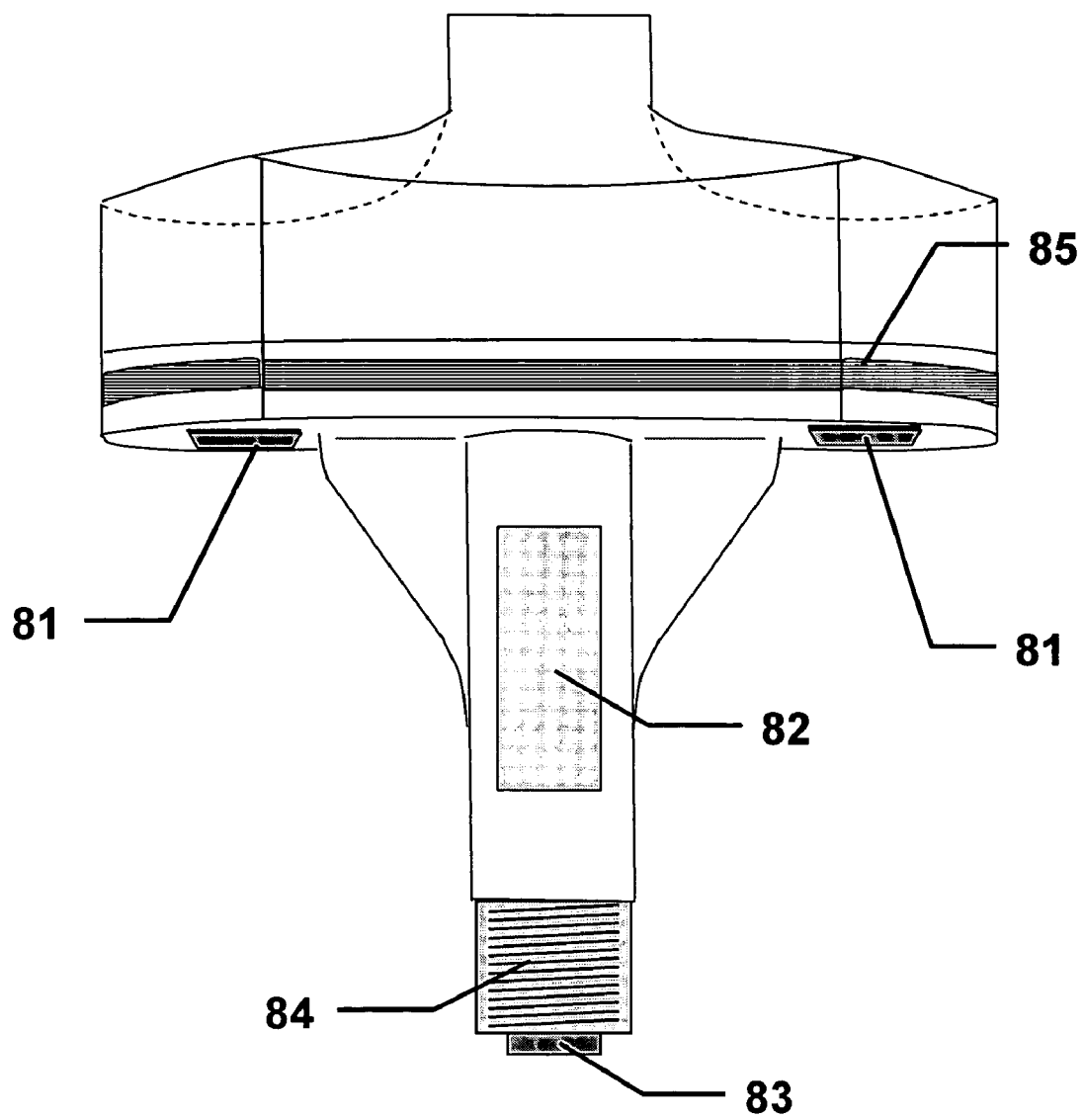
FIG. 8 is an illustration of a self-powered diagnostic device in a tibial prosthesis.

FIG. 8 is an embodiment schematic of a self-powered instrumented tibia wherein a tray sensor package 81 for loads, vibrations, temperature, and infections is disposed underneath the tibial tray. A signal processor 82 is disposed in the post of the device with an intramedulary sensor package 83 disposed on the tip of the antennae 84. The intramedulary package 83 comprises sensors for infection, temperature, and vibrations. A piezoelectric layer 85 is used to power the device.

Figure 4:
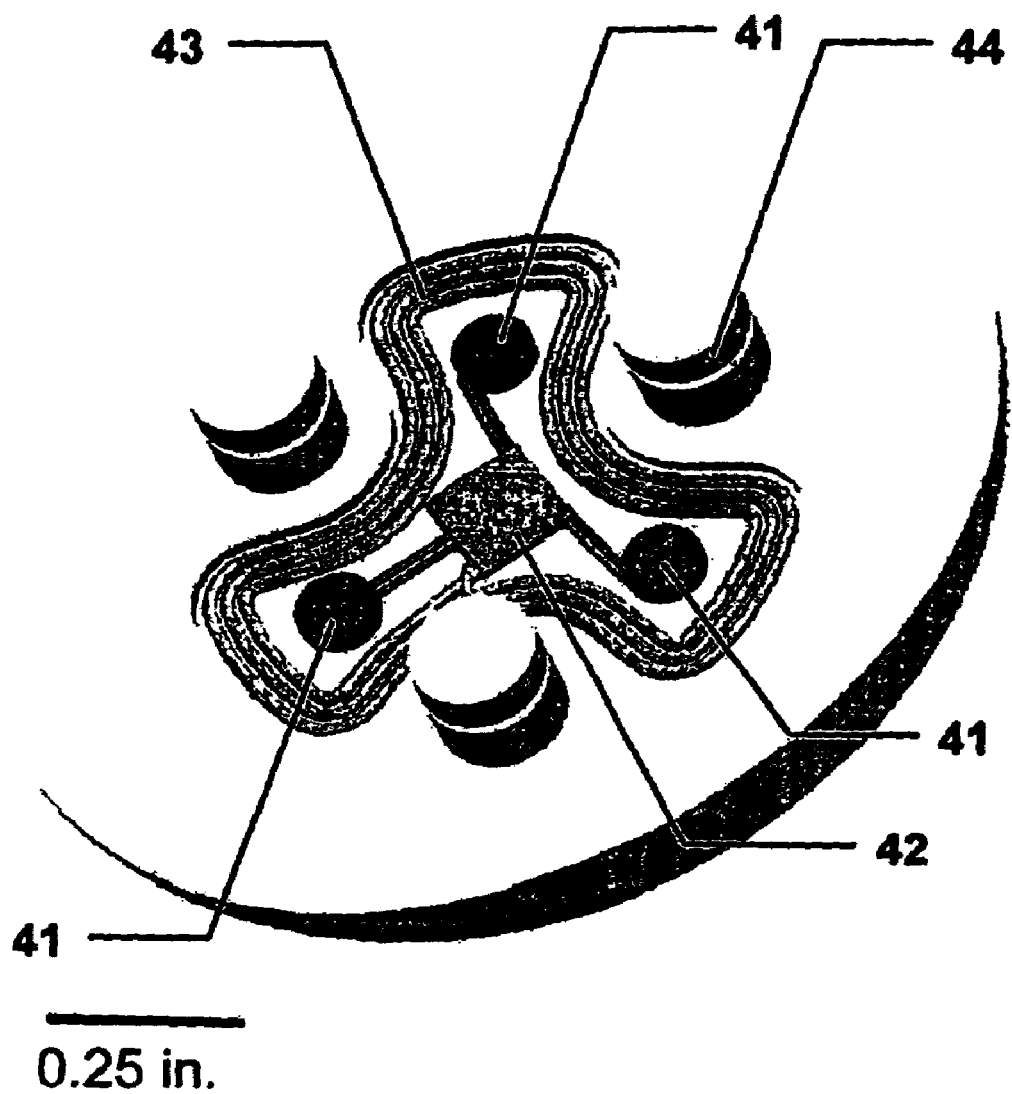
FIG. 4 is a schematic diagram of an externally powered load cell.

FIG. 4 is a patellar sensor package embodiment having microcantilever sensors 41 in communication with a signal processor 42 that is powered from an induction coil 43. Patellar studs 44 are used for mounting. The power source could be external electromagnetic induction (not shown), external radio frequency induction (not shown) or rechargeable batteries (not shown).

Figure 5:
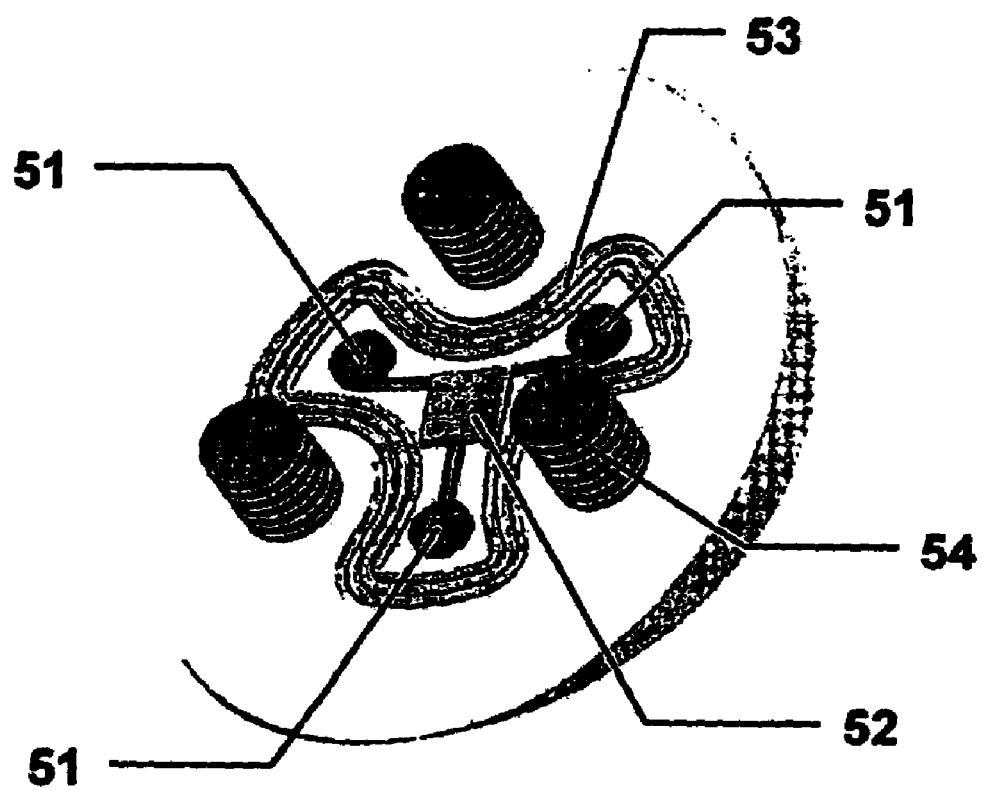
FIG. 5 is a schematic diagram of a self-powered load cell.

FIG. 5 is a patellar self-powered sensor package embodiment having microcantilever sensors 51 in communication with a signal processor 52 that is powered from an induction coil 53. The power source could be piezoelectric stacks 54, external electromagnetic induction (not shown), external radio frequency induction (not shown) or rechargeable batteries (not shown).

The infection sensing portion of the invention represents a significant advancement in the understanding of cellular signaling processes, and the maturation of technology for investigation of interactions between micro-electromechanical devices and organic tissue. Drug-discovery experiments have been performed using aptamers and fluorescent labeling to detect cancer cells, HIV, and indicators of other diseases, and aptamers have been suggested for the investigation of other inflammatory diseases such as rheumatoid arthritis and osteoarthritis. This invention has general application to the investigation of drug delivery and the general treatment of disease.

In order to detect the presence of infection, this invention detects the body's earliest response mechanisms to infection rather than attempting to detect specific bacterial or viral elements. An array of sensing elements determines the presence of several indicators of infection in order to have redundancy in the detection scheme. The cytokine response spectrum, or other inflammatory chemicals typically associated with infection, is measured and used to determine information about the type of infection present. The primary method of detection is using microcantilevers functionalized with aptamers or antibodies specific to several cytokine proteins or other inflammatory chemicals. These elements will detect changes in the in vivo environment, and the presence of proteins used in cellular communications. Part of this approach is based on microcantilever sensing technologies and use microcantilever arrays coated with cytokine receptors to detect the concentration of cytokines.

This invention uses aptamer nucleotides and antibodies with affinities to cytokines. In the case of aptamers, functional groups may be added to these aptamers to promote binding to microcantilever substrates, and a series of nucleotides combined with linking elements are used. C-reactive protein antibodies may also be used as a general indicator of pro-inflammatory cytokines. An array of microcantilevers is functionalized with the c-reactive protein antibodies and DNA aptamer materials. The response of these arrays is characterized and calibrated using known quantities of cytokine proteins.

These arrays of microcantilevers are utilized for in vitro tissue culture experiments in which endothelial, mast, neutrofil, macrophage, osteoblast, and osteoclast cells are stressed by common bacterial and viral infectious agents (*Staphylococcus epidermidis, Staphylococcus aureus, Peptostreptococcus* sp., *Proteus* sp., *Escherechia coli, Enerococcus*, Hepatitis B and C virus, etc.). The cytokine response of the various cellular signaling agents is determined under the controlled in vitro conditions. This invention also provides information on the compatibility of the sensors with biological materials.

Effective packaging and communication of biological information to processing elements is necessary; however these requirements are not as strict as they would be for longer term implantation. The packaging contains the sensing elements, provides physical protection, controls the diffusion of analytes, and protects the sensing elements from attack by the immune system. For this latter task, a suitable membrane is used to reduce the degradation of sensor performance by contaminants (e.g., immunoglobins) over short periods of time. Furthermore, the entire package is biocompatible.

Transmitting biosensor information to a suitable processing element is another requisite for in vivo sensing. Telemetry is a preferred mechanism for data transmission. It can be miniaturized to greatly increase user convenience. Percutaneous wires are another method for transmitting of cellular signaling information, and would be adequate for short-term testing.

A set of uncoated cantilevers is included in the sensor suite to measure vibrational forces and dynamic accelerations. The measurement of internal vibrations is used to determine if joint loosening has occurred. Early diagnosis of implant loosening is often difficult to determine from use of routine radiographs. The longer the delay in diagnosis of implant loosening, the greater the bone loss created from frictional abrasion of bone from motion of the loose components. Therefore, any sensing device which would signal early prosthetic loosening would result in bone preservation, and theoretically, higher success rates of revision total joint arthroplasty because more bone is available for revision implant fixation. The impacting of the joint components will cause large jumps in the vibration frequencies measured by this system. If the natural frequency of the prosthesis is similar to the frequencies encountered during ordinary activities, this can cause loosening of the prosthetic joint, excessive wear of the prosthetic joint and eventual failure of the prosthesis.

Several methods are available to power the sensor remotely. Remote power can be used to power the system for operation in a totally passive mode (the system only operates when a remote power source is available), or remote power coupling can be used to recharge internal batteries. In the preferred embodiment, the sensor is powered remotely using magnetic or RF induction. The analog data from the sensor will be converted to frequency and will be transmitted using a low-power RF transmitter.

A self-powered version of this system, as shown in FIG. 5, uses a self-power generating system comprising substituting stacks 54 of piezoelectric material for the mounting studs of the patella. Layers of piezoelectric materials can also be incorporated in other orthopedic devices for self-powered applications, such as incorporating thin layers of piezoelectric material underneath the polyethylene portion of the tibial tray, as shown in FIG. 8, or in the mounting locations of the femoral component. The forces from everyday activities are sufficient to charge a small battery or a capacitive storage system.

While there has been shown and described what are at present considered the preferred embodiments of the invention, it will be obvious to those skilled in the art that various changes and modifications can be made therein without departing from the scope.

We claim:

1. A device for providing in vivo diagnostics of loads, wear, and infection in orthopedic implants, said device comprising:
    at least one load sensor associated with said implant, said at least one load sensor for generating an output signal in response to and indicative of normal and transverse loads being applied to said implant; and
    at least one temperature sensor associated with said implant, said at least one temperature sensor for generating an output signal in response to and indicative of a temperature proximate said implant; and
    at least one vibration sensor associated with said implant, said at least one vibration sensor for generating an output signal in response to and indicative of a vibration proximate said implant; and
    at least one signal processing device operatively coupled with said at least one load, temperature, and vibration sensor, said at least one signal processing device being operable to receive said output signal from said at least one load, temperature, and vibration sensor and to transmit a signal corresponding with said output signal.

2. The device of claim 1 wherein said at least one load, temperature, and vibration sensor further comprises a microelectromechanical system.

3. The device of claim 2 wherein said microelectromechanical system further comprises at least one element selected from the group consisting of piezoelectric material, double supported microbeam, piezoresistive coating, piezoelectric coating, and parallel plate capacitor.

4. The device of claim 1 wherein said device is powered by a power supply comprising at least one device selected from the group consisting of piezoelectric elements, piezoelectric stacks, electromagnetic induction, radio frequency induction and rechargeable batteries.

5. The device of claim 1 wherein said at least one load, temperature, and vibration sensor further comprises at least one encapsulant selected from the group consisting of polymer and elastomeric material.

6. The device of claim 5 wherein said encapsulant further comprises a convex surface and a concave surface.

7. The device of claim 1 wherein said device is disposed in at least one component selected from the group consisting of tibia, fibia, femora, patella, acetabula, scapula, humera, talus, and intervertebral space.

8. The device of claim 1 wherein said signal processing device further comprises at least one transmission device selected from the group consisting of wireless telemetry and percutaneous wiring.

9. A device for providing in vivo diagnostics of loads, wear, and infection in orthopedic implants, said device comprising:
- at least one load sensor associated with said implant, said at least one load sensor for generating an output signal in response to and indicative of a normal and transverse loads being applied to said implant;
- at least one temperature sensor associated with said implant, said at least one temperature sensor for generating an output signal in response to and indicative of a temperature proximate said implant;
- at least one vibration sensor associated with said implant, said at least one vibration sensor for generating an output signal in response to and indicative of a vibration proximate said implant;
- at least one ultrasonic device associated with said implant, said at least one ultrasonic device for generating an output signal in response to and indicative of wear being imposed on said implant; and
- at least one signal processing device operatively coupled with said at least one load sensor, temperature sensor, vibration sensor, and ultrasonic device, said at least one signal processing device being operable to receive said output signal from said at least one load sensor, temperature sensor, vibration sensor, and ultrasonic device and to transmit a signal corresponding with said output signal.

10. The device of claim 9 wherein said at least one load sensor, temperature sensor, vibration sensor, and ultrasonic device further comprises a microelectromechanical system.

11. The device of claim 10 wherein said microelectromechanical system further comprises at least one element selected from the group consisting of piezoelectric material, double supported microbeam, piezoresistive coating, piezoelectric coating, and parallel plate capacitor.

12. The device of claim 9 wherein said device is powered by a power supply comprising at least one device selected from the group consisting of piezoelectric elements, piezoelectric stacks, electromagnetic induction, radio frequency induction and rechargeable batteries.

13. The device of claim 9 wherein said at least one load sensor, temperature sensor, vibration sensor, and ultrasonic device further comprises at least one encapsulant selected from the group consisting of polymer and elastomeric material.

14. The device of claim 13 wherein said encapsulant further comprises a convex surface and a concave surface.

15. The device of claim 9 wherein said device is disposed in at least one component selected from the group consisting of tibia, fibia, femora, patella, acetabula, scapula, humera, talus, and intervertebral space.

16. The device of claim 9 wherein said signal processing device further comprises at least one transmission device selected from the group consisting of wireless telemetry and percutaneous wiring.

17. A device for providing in vivo diagnostics of loads, wear, and infection in orthopedic implants, said device comprising:
- at least one load sensor associated with said implant, said at least one load sensor for generating an output signal in response to and indicative of a normal and transverse loads being applied to said implant; and
- at least one temperature sensor associated with said implant, said at least one temperature sensor for generating an output signal in response to and indicative of a temperature proximate said implant;
- at least one vibration sensor associated with said implant, said at least one vibration sensor for generating an output signal in response to and indicative of a vibration proximate said implant; and
- at least one ultrasonic device associated with said implant, said at least one ultrasonic device for generating an output signal in response to and indicative of wear being imposed on said implant;
- at least one chemical sensor associated with said implant, said at least one chemical sensor for generating an output signal in response to and indicative of infection proximate said implant; and
- at least one signal processing device operatively coupled with said at least one load sensor, temperature sensor, vibration sensor, ultrasonic device, and chemical sensor said at least one signal processing device being operable to receive said output signal from said at least one load sensor, temperature sensor, vibration sensor, ultrasonic device, and chemical sensor and to transmit a signal corresponding with said output signal.

18. The device of claim 17 wherein said at least one load sensor, temperature sensor, vibration sensor, ultrasonic device, and chemical sensor further comprises a microelectromechanical system.

19. The device of claim 18 wherein said microelectromechanical system further comprises at least one element selected from the group consisting of piezoelectric material, double supported microbeam, piezoresistive coating, piezoelectric coating, parallel plate capacitor, antibody coating, and aptameric receptor coating.

20. The device of claim 19 wherein said antibody coating is specific to at least one attractant selected from the group consisting of c-reactive proteins, activated factor XII, serotonin, and epinephrine.

21. The device of claim 19 wherein said aptameric receptor coating is specific to at least one cytokine selected from the group consisting of tumor necrosis factor-•, interleukin-1, interleukin-6, and interferon.

22. The device of claim 17 wherein said device is powered by a power supply comprising at least one device selected from the group consisting of piezoelectric elements, piezoelectric stacks, electromagnetic induction, radio frequency induction and rechargeable batteries.

23. The device of claim 17 wherein said at least one load sensor, temperature sensor, vibration sensor, ultrasonic device, and chemical sensor further comprises at least one encapsulant selected from the group consisting of polymer and elastomeric material.

24. The device of claim 23 wherein said encapsulant further comprises a convex surface and a concave surface.

25. The device of claim 17 wherein said device is disposed in at least one component selected from the group consisting of tibia, fibia, femora, patella, acetabula, scapula, humera, talus, intervertebral space, and tissue.

26. The device of claim 17 wherein said signal processing device further comprises at least one transmission device selected from the group consisting of wireless telemetry and percutaneous wiring.

27. The device of claim 17 wherein said chemical sensor further comprises at least one bacteria sensor disposed in drainage tube effluent.

28. A method for providing in vivo diagnostics of loads, wear, and infection in orthopedic implants comprising the steps of:
  positioning a sensor suite proximate an orthopedic implant, said sensor suite further comprising at least one device selected from the group consisting of load sensor, temperature sensor, vibration sensor, ultrasonic device, and chemical sensor,
  powering said sensor suite for collecting and transmitting data,
  analyzing said data to determine loads, wear, and infection in said orthopedic implant.

29. The method of claim 28 wherein said at least one load sensor, temperature sensor, vibration sensor, ultrasonic device, and chemical sensor further comprises a microelectromechanical system.

30. The method of claim 29 wherein said microelectromechanical system further comprises at least one element selected from the group consisting of piezoelectric material, double supported microbeam, piezoresistive coating, piezoelectric coating, parallel plate capacitor, antibody coating, and aptameric receptor coating.

31. The method of claim 30 wherein said antibody coating is specific to at least one attractant selected from the group consisting of c-reactive proteins, activated factor XII, serotonin, and epinephrine.

* * * * *